United States Patent
D'Acchioli et al.

(10) Patent No.: US 6,551,292 B1
(45) Date of Patent: *Apr. 22, 2003

(54) SHAPED FLANGE FOR A URINE COLLECTOR

(75) Inventors: Vincenzo D'Acchioli, Kelkheim/Ts. (DE); Gianfranco Palumbo, Bad Homburg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/720,174

(22) PCT Filed: Jun. 28, 1999

(86) PCT No.: PCT/US99/14608

§ 371 (c)(1),
(2), (4) Date: Dec. 20, 2000

(87) PCT Pub. No.: WO00/00116

PCT Pub. Date: Jan. 6, 2000

(51) Int. Cl.[7] ................................................ A61F 13/15
(52) U.S. Cl. ................. 604/329; 604/385.01; 604/317; 604/338; 604/339
(58) Field of Search ................................ 604/317–356, 604/357–412

(56) References Cited

U.S. PATENT DOCUMENTS

| | | | |
|---|---|---|---|
| 3,368,561 A | 2/1968 | Ericson et al. | |
| 3,577,989 A | * 5/1971 | Anderson | 128/283 |
| 4,804,377 A | 2/1989 | Hanifl et al. | 604/352 |
| 5,417,680 A | * 5/1995 | Kimura et al. | 604/385.2 |
| 6,350,256 B1 | * 2/2002 | Palumbo et al. | 604/339 |

FOREIGN PATENT DOCUMENTS

| | | |
|---|---|---|
| EP | 0 887 063 | 12/1998 |
| FR | 2 619 504 | 2/1989 |
| GB | 1 092 274 | 11/1967 |
| GB | 1 422 638 | 1/1976 |
| GB | 2 015 347 | 9/1979 |

* cited by examiner

*Primary Examiner*—Jeanette Chapman
(74) *Attorney, Agent, or Firm*—Larry L. Huston; Ian S. Robinson

(57) ABSTRACT

The present invention relates to a female adult urine management device (10) designed to provide improved body fit between the flange and the skin of the wearer and thereby prevent leakage. The urine management device (10) comprises a bag (11) having an aperture (13), and a flange (12), which surrounds the aperture (21). The flange (12) provides for adhesive attachement to the uro-genital area of the wearer. In particular, the rear portion (46) of the flange comprises a projection (48), which provides an effective seal between the flange (12) and the skin of the wearer and prevents leakage to the urinary tract. In particular the device (10) fits snugly between the labia and the anus and thereby improves sealing. In another aspect of the present invention, projection acts as a application to assist in the easy and correct positioning of the device.

10 Claims, 4 Drawing Sheets

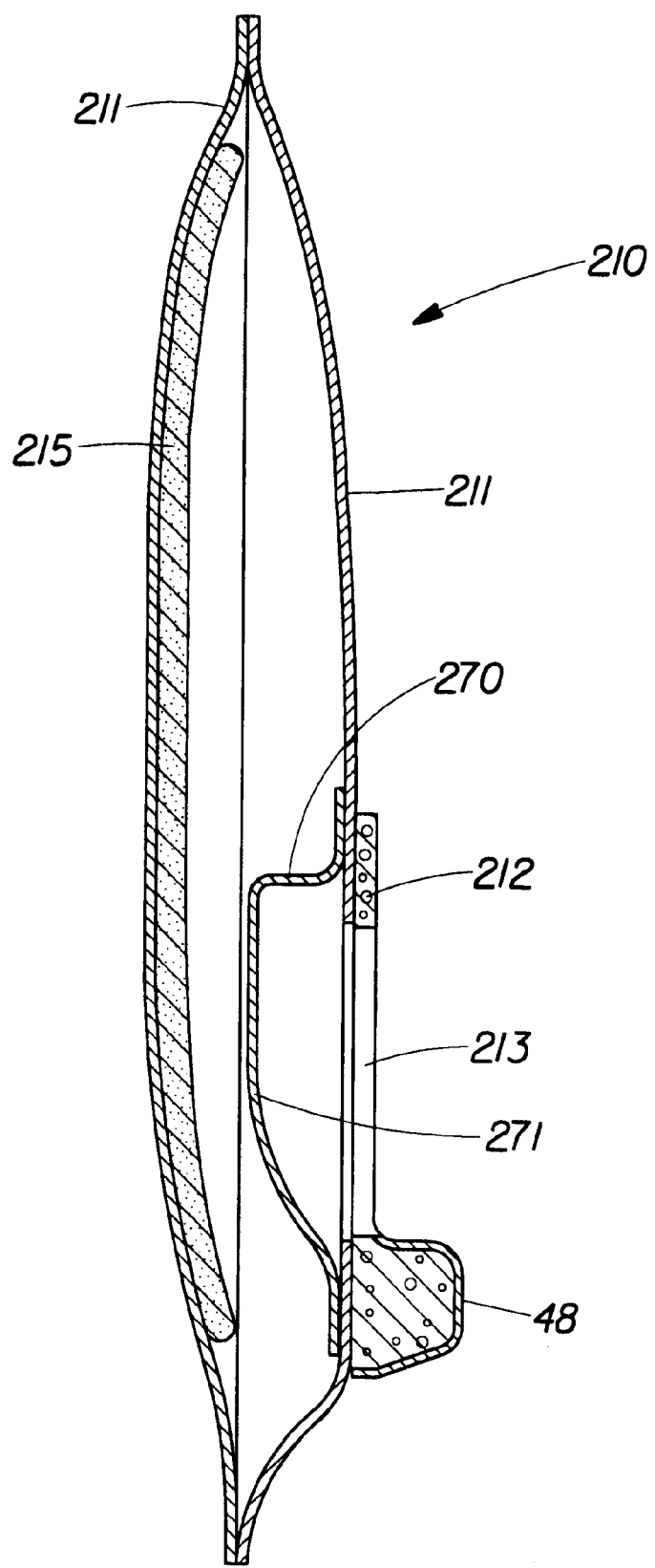

SHAPED FLANGE FOR A URINE COLLECTOR

CROSS REFERENCE

This application claims priority to PCT International Application Serial No. PCT/US99/14608 filed on Jun. 28, 1999 which claims priority to European Patent Application No. 98124491.6 filed on Dec. 28, 1998, which claims priority PCT International Application Serial No. PCT/US98/13288 filed on Jun. 26, 1998, and PCT International Application Serial No. PCT/US98/13289 filed on Jun. 26, 1998.

FIELD OF THE INVENTION

The present invention relates to a body fitting urine management device. In particular, the present invention is directed towards urine management devices with improved skin attachment means such that improved body fit and a tight seal is provided between the body of the wearer and the skin, thereby preventing leakage and contact between the feacal material and the urinary tract and thus preventing urinary tract infections. The devices find particular utility for adult female wearers of such devices.

BACKGROUND OF THE INVENTION

Urine management devices are known articles of manufacture that are designed to be worn principally by incontinence sufferers and infants. Such urine management devices are attached to the urogenital region of the wearer and are intended to entrap and immediately contain urine and other bodily discharges. As a consequence, these devices are functionally effective in lessening epidermal irritation; in preventing contamination of articles such as clothing and bedding; and even in preventing the soiling of the carers themselves.

Typically, the urine management devices are made from a plastic bag material and an adhesively faced attachment member joined to the bag. For instance, GB 1,092,274 discloses a paediatric urine collector for female use comprising a collector bag of plastic material opening for collection of urine for analysis. The base of the opening is provided with a wedge like projection adapted to engage the lower perineal area of the infant. The collector is secured to the body of the wear by adhesive material. Similarly U.S. Pat. No. 4,804,377 discloses a urine collector having a urine collection bag with a urine inlet and an adhesively faced attachment member. The attachment member is further provided with a bulge shape to span the perineum of the infant wearer. The urine collection devices are designed to collect urine typically for analysis and thus must be of sufficient dimension to contain a full discharge and are therefore bulky. Furthermore they are not designed to be worn for any length of time next to the body or to be worn in inside a diaper or undergarment.

There hence still exists a need to provide a urine management device which is designed to perfectly fit and conform to the an adult wearer. In particular there is a need to provide a urine management device for adult wearers which provides a seal between the device and the wearer such that leakage will not occur even when the wearer is active. Moreover it is particularly desirable to provide a urine management device for female adult wearers which prevents the ingress of faecal matter or bacteria into the urinary tract, and which prevents the ingress of urine and bacteria from the urinary tract to the anal region of the wearer.

Another problem related to currently available urine management devices is the ease of placement of the device in the correct position. Adult wearers suffering from incontinence may also be afflicted by other disabilities such that they require an easy means to guide the device into the correct position required. Obviously removal and reapplication of the device is most undesirable particularly on the sensitive genitalia area which may be already irritated due to the incontinence problem and thus correct first time positioning is also highly desirable.

The present invention addresses these needs by providing a projection at the rear portion of the flange. It has been found that the presence of such a projection is uniquely advantageous and prevents the flow of urine material out of the rear portion of the flange and prevents the flow of faecal material from the anus towards the urinary tract. Furthermore, the presence of such a projection on the urine management device causes no discomfort to the wearer, leads to a great reduction in infections and epidermal irritations derived from faecal material and bacteria and results in a high level of wearer and carer satisfaction in relation to skin healthiness. In addition the projection also assist in providing the wearer or caretaker with an application aid to guide the device into the correct position.

In another aspect of the present invention, the urine management device with this projection can be advantageously used with a disposable adult incontinence diaper and or a faecal management device.

SUMMARY OF THE INVENTION

A urine management device constructed in accordance with the present invention comprises a bag having an aperture and a flange surrounding the aperture for adhesive attachment to the uro-genital area of the wearer. The anatomically-shaped flange is attached to the bag and comprises an outer periphery, an inner periphery adjacent to the aperture, a longitudinal centreline and a transverse centreline wherein the transverse centreline segments the flange into a front portion and a rear portion.

In particular, the flange comprises a projection in the rear portion. The projection is disposed between the outer periphery and the inner periphery of the flange in a direction parallel to the longitudinal direction. Preferably, the projection extends from the outer periphery to the inner periphery and is disposed in a symmetrical manner. The projection has an effective height ranging from 5 millimeters to 30 millimeters, preferably from 10 millimeters to 20 millimeters, more preferably an effective height of about 12 to 20 millimeters, moat preferably 15 millimeters. The projection is particularly beneficial for female wearers where the projection is are adapted to fit snugly between the labia and the anus, i.e., the perineum of the female wearer.

In another aspect of the present invention, the present urine management device is used in combination with a disposable adult incontinence diaper and or with a faecal management device.

A further aspect of the invention relates to the use of said projection as an application aid to ensure ease of placement and ideal positioning of the device.

A yet further aspect of the invention relates to the use of said projection to prevent leakage of the liquids entering or stored within the device.

A further aspect of the invention relates to the use of said projection for the prevention of urinary tract infections.

BRIEF DESCRIPTION OF THE DRAWINGS

It is believed that the invention will be better understood from the foregoing description in conjunction with the accompanying drawings in which:

FIG. 4 is a cross-sectional view of another embodiment of a disposable urine management device of the present invention.

DETAILED DESCRIPTION OF THE INVENTION

Figure 1:
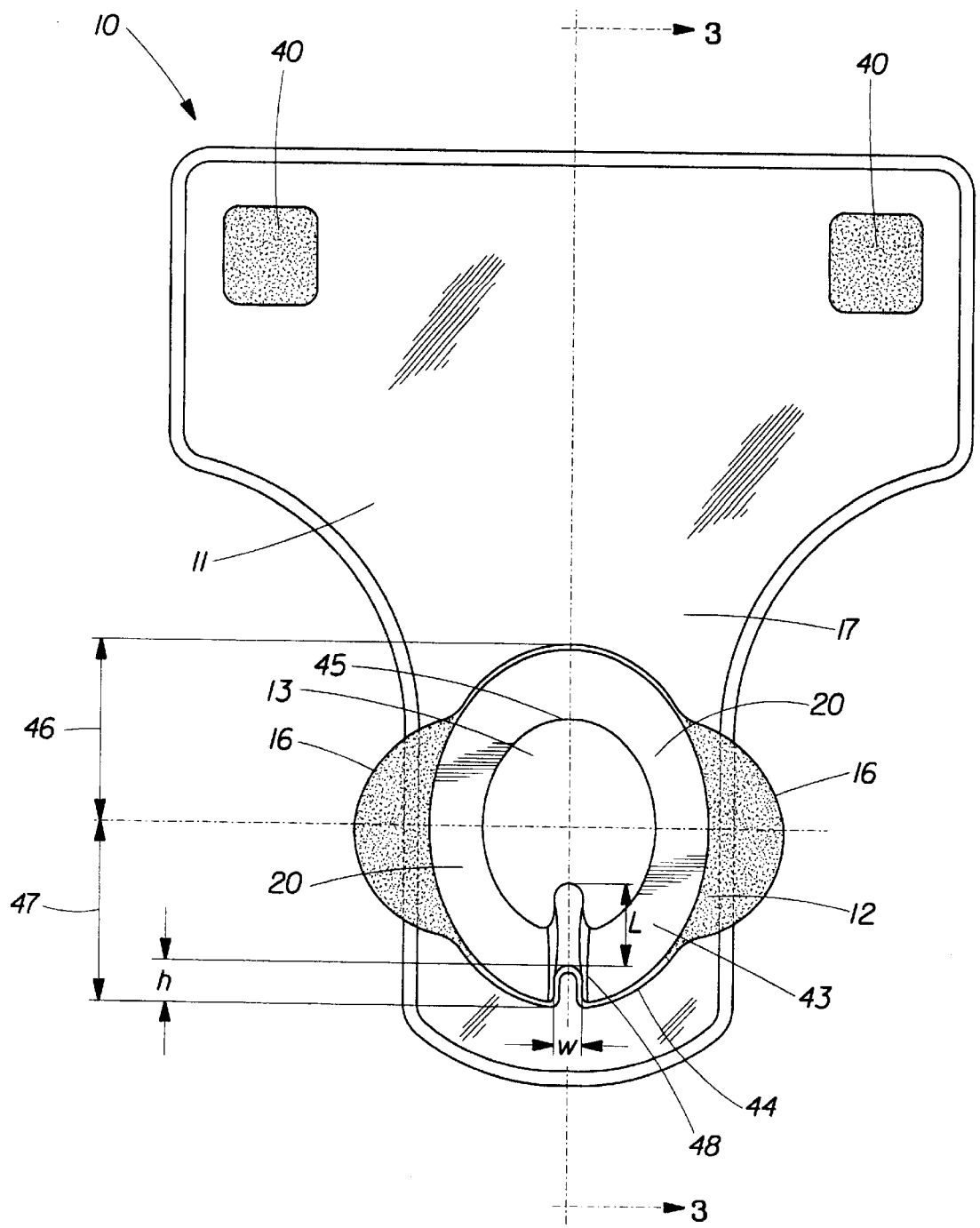
FIG. 1 is a plan view of a disposable urine management device of the present invention.

According to FIG. 1, the urine management device (10) of the present invention comprises a bag (11) having an aperture and a flange (12) surrounding the aperture (21) for adhesive attachment to the skin of the wearer in the uro genital area of the wearer.

From FIG. 1, it is evident that the anatomically-shaped flange (12) comprises an outer periphery (44), an inner periphery (45) adjacent to and defining an aperture (13), a longitudinal centreline L and a transverse centreline T orthogonal thereto. The transverse centreline T segments the anatomically shaped flange (12) into a front portion (46) and a rear portion (47). The flange (12) further comprises a wearer facing surface (43) and a garment facing surface (42).

According to the present invention it has been surprisingly found that the presence of a projection (48) positioned on the wearer facing surface of the anatomically shaped flange (12) as described herein after is particularly beneficial. The projections are firstly particularly effective in reducing and preventing any urine matter from escaping from the device (10) between the skin and the flange and from preventing any contact of faecal matter and or bacteria with the urinary tract and genital organs. It is believed that the positioning of such a projection (48) at the rear portion (46) of the wearer facing surface of the flange (43) not only provides a flange which more readily conforms to the contours of anatomy of the body, but also provides an improved seal. In addition, a further surprising advantage of the present invention is that the presence of the rear projection (48) also functions as a application aid to the wearer or caretaker who applies the device. Using the projection the caretaker or wearer is not only provided with an easily graspable element of the device to hold, but also can use the projection to guide the device into the correct wearing position i.e. between the labia and the anus, further improving the sealing benefit. This is particularly useful for female wearers where the projection may be inserted into the urethra.

According to the present invention the projection is disposed between the outer periphery (44) and the inner periphery (45) of the anatomically-shaped flange (12) in a direction parallel to the longitudinal direction L. In addition the projection also extends in the transverse direction between the longitudinal side edges on either side of the longitudinal centreline L. More preferably, the flange (12) extends from the outer periphery (44) to the inner periphery (45). In the transverse direction, the projection (48) preferably does not extend across the entire transverse width of the flange but only up to 50% of the width more preferably up to 30% of the width of the flange measured through the centre of the projection.

The rear projection (48) may be disposed symmetrically or asymmetrically about the longitudinal centreline L. In a more preferred embodiment, the projection (48) is disposed in a substantially symmetrical manner. According to the present invention the projection (48) extends perpendicular to the plane of the flange. It is important that the projection (48) be upstanding and rise above the plane of the flange (12) to an effective height H sufficient to present an abrupt discontinuity to obstruct the movement of the urine or faecal material. As used herein, the term "effective height" refers to the maximum distance in the Z-direction from the garment facing (42) of the flange (12) in its flat orientation of the projection, including adhesive if present on the projection surface. The projection (48) have an effective height (h) ranging from 5 millimeters to 30 millimeters. Preferably, the projection (48) has an effective height ranging from 10 millimeters to 20 millimeters, more preferably an effective height of about 12 millimeters to 20 millimeters, most preferably 15 millimeters. The effective height measurements are carried out without the aid of a micrometer in order that no pressure is exerted onto the adhesive and flange material. Typically, the projection (48) is orthogonal to the plane of the flange (12). It should be recognised however that if the flange (12) has wrinkles, rugosities, undulations or other deviations from planarity, these should be taken into account at the position of the projection (48), when determining its effective height. The projection also preferably has a length (l) extending between the outer periphery (44) of the flange to the inner periphery (45) of the flange measured at the longest point of from 5 millimeters to 40 millimeters, preferably from 10 millimeters to 30 millimeters, more preferably from 15 millimeters to 25 millimeters, most preferably 20 millimeters. The projection also has a preferred width (w) which is measured at the midway point of the effective height of from 3 millimeters to 20 millimeters, preferably from 5 millimeters to 10 millimeters, most preferably 8 millimeters.

According to the present invention the projection (48) may have any shape. Typically the projection (48) has a longitudinal and or transverse substantially convex cross section. The front projection (48) is typically independently convex in shape and provides a hump-like or hill-like longitudinal cross section and or transverse cross section or provides a tubular cross section. The projection may also have a dual humplike cross section, so as to provide a projection (48) having two or more distinct heights. Preferably, the hump exhibiting the maximum or effective height of the projection will be positioned towards the outer periphery (44) of the flange (12).

The projection (48) is preferably hollow or partially hollow to improve resiliency and flexibility of the projection but may also be completely filled. For embodiments wherein the projection (48) is hollow or partially hollow, the projection may require additional support means in order to maintain the desired resilient configuration of the projection (48). Suitable support means include adhesives or the provision of an elastic material connecting the longitudinal sides of the projection (48) to oneanother at least the base of the projection (48) on the wearer facing surface (43) of the flange (12).

According to the present invention the projection (48) should preferably be laterally compressible so that the projection will move inward when compressed by lateral forces rather than spring back. The projection (48) should also be resiliently deformable such that if for example the longitudinal sides are compressed the upper or top portion of the projection will be forced upwards and thereby provide a vertical extension of the projection in use and increase the overall effective height of the device. In this manner the sealing effect provided by the projection (48) and more preferably in combination with the flange (12) and adhesive (20) is always maintained, even when the wearer of the device is active during use and thereby places increased pressure onto the device.

The projection (48) may be formed as an integral part of the flange or may be provided as separate entities whereby a material which may be different or identical to the flange material is attached to the flange (12) using means known in the art, typically adhesive. Preferably however, the projection (48) is formed as an integral part of the flange. The projection (48) may be made by forming a single pleat in the constituent material of the flange (12) or by thermobonding the flange material. Alternatively, the projection (48) may be provided by a body compatible adhesive material. In a preferred embodiment of the present invention however, the projection (48) is formed from the flange material itself and utilises an adhesive support means.

The projection (48), may either be coated with adhesive or be substantially free from adhesive. According to a preferred embodiment of the present invention, the projection (48) is also covered with a body-compatible adhesive. For embodiments wherein the projection (48) comprises a dual hump longitudinal cross section for example, it has been found particularly beneficial to provide only one of the surfaces of the hump, preferably the hump providing "the effective height" with a body compatible adhesive. The remaining hump surface may be provided with an anti slip material such as rubber.

The term "disposable" as used herein describes devices which generally are not intended to be laundered or otherwise restored or reused (i.e., they are intended to be discarded after a single use and, preferably, to be recycled, composted or otherwise disposed of in an environmentally compatible manner).

Figure 2:
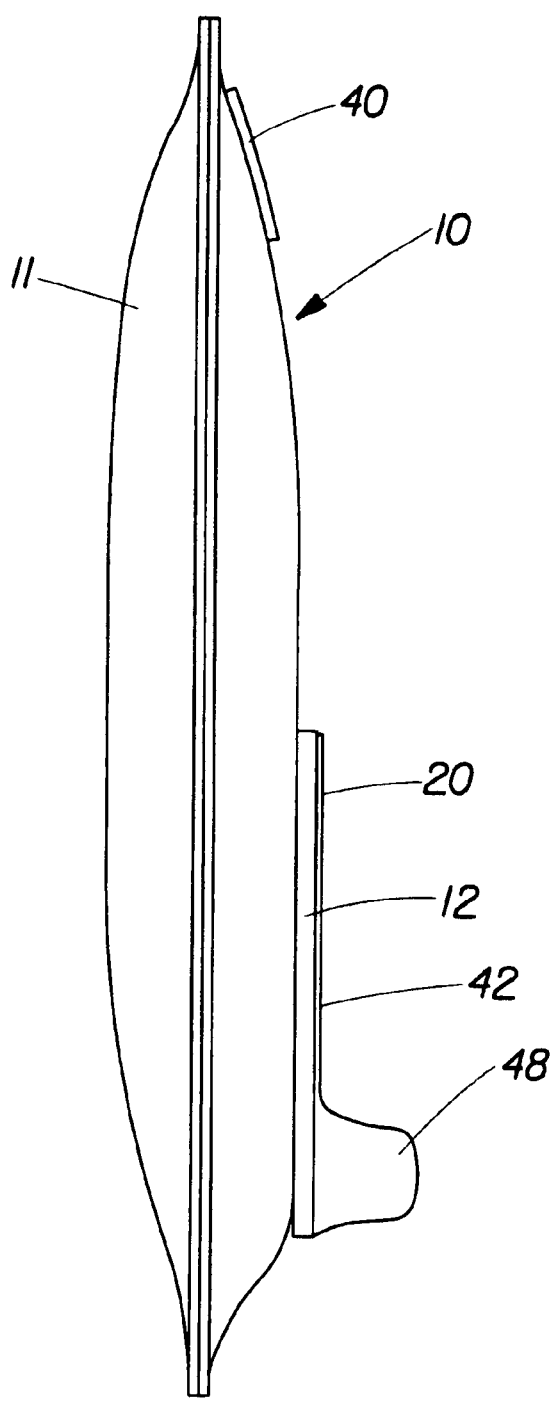
FIG. 2 is a side view of the disposable urine management device of FIG. 1.
Figure 3:
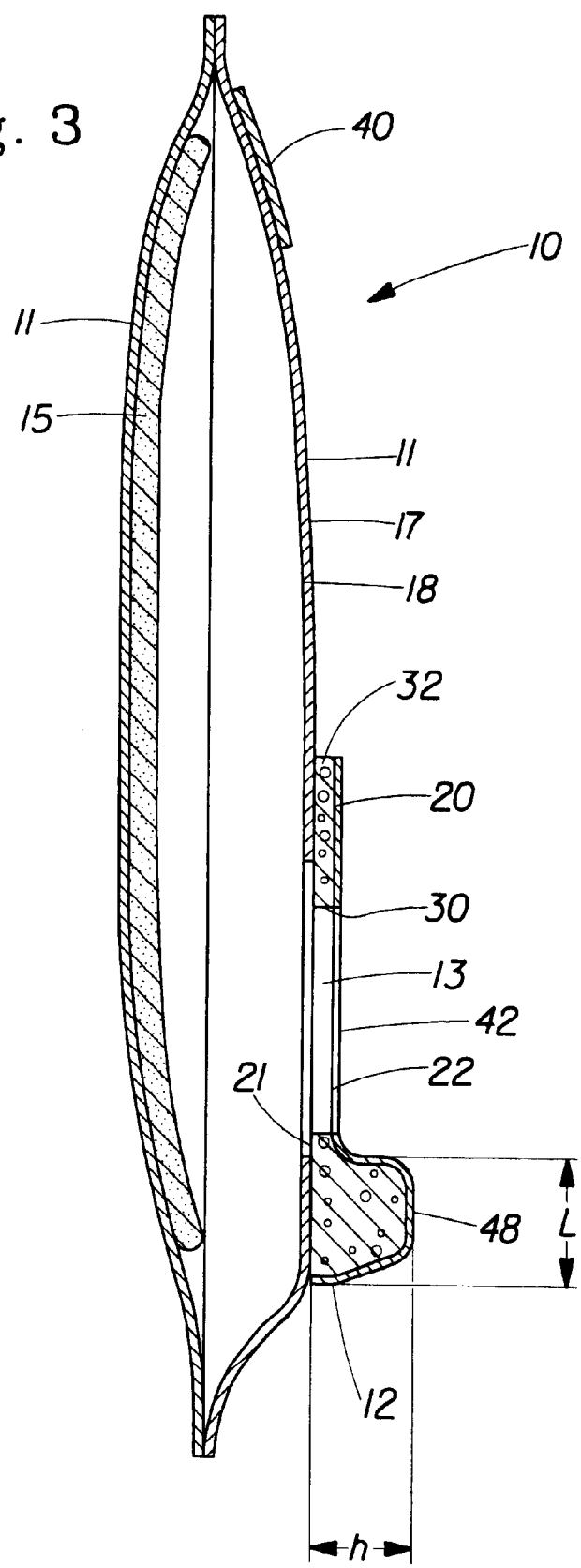
FIG. 3 is a cross-sectional view taken along line 3—3 of FIG. 1.

Referring now to FIGS. 1–3, there is shown a urine management device (10). Typically disposable urine management devices (10) comprise a bag (11) having an aperture (13) and a flange (12) surrounding the aperture (13) for preferably adhesive attachment to the uro-genital area of a wearer. Any urine management device (10) known in the art can be provided according to the present invention.

The bag (11) as used herein is a flexible receptacle for the containment of discharged urine matter. The bag (11) can be provided in any shape or size depending on the intended use thereof, i.e. whether the device is intended for bedridden patients or active patients suffering from incontinence or for infants. For example elongated bags which are principally tubular or rectangular are typically utilised by bedridden patients and elderly incontinence sufferers. For more active wearers whether infants or adults, the urine management device should preferably be anatomically shaped such that the device follows the contours of the body and can be worn inconspicuously by the wearer under normal garments.

Particularly, preferred shapes are flat circular and flat T shaped type bags, cone shaped bags, truncated cone shaped bags and pyramidal or truncated pyramidal shaped bags. In a most preferred embodiment of the present invention, the bag (11) has a substantially flat T shape.

In addition, the bag (11) is preferably shaped to fit the urogenital region of the wearer and ensure good contact between the flange and the skin of the wearer. For example the bag (11) may be provided with a neck portion or conduit.

The bag (11) is preferably designed to provide sufficient volume for urine under a variety of wearing conditions, also when worn by a freely moving, i.e. not bedridden wearer.

The bag (11) is designed to safely contain any entrapped material, typically it will be liquid impermeable, yet it may be breathable. The bag (11) is designed of sufficient strength to withstand rupture in use, also when pressure on the bag (11) is exerted.

According to the present invention, depending on the shape of the bag (11) required, the bag (11) may be provided from a unitary piece of material or from a number of separate pieces of material, which may be identical or different and which are sealed at their respective peripheries.

According to the present invention the bag (11) can comprise one or multiple layers, preferably two or three layers. The layer on the inside of the bag, which will typically at least partially come in contact with urine and or other bodily excretions is called the inner layer (18). The outermost layer of the bag, which will typically at least partially come in contact with the skin to the wearer and the garments of the wearer, is called the outer layer (17).

The layers of the bag material may be provided from any material, preferably so that the bag is liquid impervious. The layers may in particular comprise any material such as nonwovens or films. In a preferred embodiment of the present invention a laminate may be formed from a nonwoven layer and a film. The laminate can be formed by means known to the man skilled in the art.

Any nonwoven layer can comprise felt fabrics, spuniaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibres or polymeric binders including natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., Ill, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag is preferably provided with a hydrophobic fibrous nonwoven layer. Such material layers present an uneven surface to the skin of the wearer and thus reduce significantly the problem of occlusion and greatly improves skin healthiness.

In one preferred embodiment of the present invention the bag comprises two layers. Preferably the outer layer (17) comprises said fibrous hydrophobic nonwoven layer and the inner layer (18) comprises a film.

In yet another preferred embodiment of the present invention, the bag (11) comprises three layers, preferably one film and two nonwoven layers. In an even more preferable embodiment the film is interposed between the two nonwoven layers. This sequence of layers results in a closed fibrous structure, which has a particularly pleasing sensation on contact with the skin of the wearer. In yet another preferred embodiment the inner layer comprises a film and the other two layers comprise nonwovens.

Typically, the nonwoven layer is treated with a surface active material, such as a fluorchemical or other hydrophobic finishings, to provide the requisite hydrophobicity. The nonwoven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The nonwoven layer can also be treated with agents to improve the tactile perceivable softness of the bag. The agents include but are not limited to vegetable, animal or synthetic oils, silicone oils and the like. The presence of these agents are known to impart a silky or flannel-like feel to the nonwoven layer without rendering it greasy or oily to the tactile sense of the wearer. Additionally, surfactant material, including anionic, non-anionic, cationic and non-cationic surfactants, may be added to further enhance softness and surface smoothness.

Furthermore, the nonwoven layer may be impregnated with a lotion to provide desirable therapeutic or protective coating lotion benefits. The lotion is transferable to the skin of the wearer by normal contact and wearer motion and/or body heat. Generally, mineral oil in the form of a lotion is recognised as being effective in imparting a soothing, protective coating to the skin of the wearer. It is also possible to impregnate the nonwoven layer with a solid oil phase of cream formulation or to incorporate into the nonwoven layer an array of pressure- or thermal- or hydrorupturable capsules containing for example, baby oil.

In one embodiment of the present invention the bag (11) may contain absorbent material (15). The absorbent material (15) may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material (15) may be positioned in the bag (11) in any suitable manner. For example, the absorbent material (15) may be loosely arranged within the bag (11) or may be secured to the inner layer of the bag (11). Any known techniques for securing absorbent material (15) to nonwoven and film substrates may be used to secure the absorbent material to the inner layer of the bag (11). The absorbent material may also be arranged to have any desired shape or configuration (e.g., rectangular, oval, circular, etc.).

In the embodiment shown in FIGS. 1–3, the outer surface of bag (11) is provided with patches of adhesive (40) for securing the bag (11) to the body of the wearer. Preferably, the patches of adhesive (40) are positioned on the outer surface of bag (11) such that they are secured to the abdomen of the wearer in use. Any number, size and shape of adhesive patches (40) may be used depending on the intended use of the device. The adhesive (40) may be any medically approved water resistant pressure sensitive adhesive such as hydrocolloid adhesives and hydrogel adhesives. Particularly effective adhesives in providing the desired adhesive properties to secure the flange to the skin of the wearer whilst allowing for relatively painless application and removal are hydrophillic hydrogels formed from crosslinking polymers with a plastisicer to form a 3-dimensional matrix.

Referring now to FIG. 4, there is shown another embodiment of a disposable urine management device (210). Disposable urine management device (210) comprises a bag (211) having an aperture (213), a flange (212) surrounding the aperture for adhesive attachment to the body of a wearer, and absorbent material (215) contained within the bag (211).

Disposable urine management device (210) also comprises an additional acquisition layer (270). Acquisition layer (270) is shown in FIG. 6 to be secured to the inner surface of bag (211). However, the acquisition layer (270) may also be secured to the flange (212), or both the flange (212) and the inner surface of bag (211). Acquisition layer (270) is preferably positioned such that it separates the genitalia of the wearer from coming into direct contact with the absorbent material (215). Acquisition layer (270) is fluid pervious allowing urine to readily pass through so that it may be absorbed by absorbent material (215).

The acquisition layer (270) may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the acquisition, barrier layer includes fibers, the fibers may be spunbond, carded, wet-laid, meltblown, hydroentangled, or otherwise processed as is known in the art.

The acquisition layer (270) is designed to have a pore size such that the absorbent material (215) is not allowed to pass through and contact the wearer's skin. While designed not to have to large of a pore size which permits the passage of absorbent material (215), the acquisition layer (270) preferably has a pore size which is greater than the pore size of the absorbent material (215).

Preferably, the acquisition layer (270) is less hydrophilic than the absorbent material (215). The acquisition layer (270) may be treated with a surfactant to increase its initial wettability. When treated with surfactant, however, the acquisition layer (270) should still be less hydrophilic than the absorbent material (215). Suitable methods for treating the acquisition layer (270) with a surfactant include spraying the acquisition layer (270) with the surfactant and immersing the material into the surfactant. Alternatively, a surfactant may be incorporated into the acquisition layer (270).

As shown in FIG. 1 the bag (11) is provided with an aperture (13) whereby urine is received from the body prior to storage within the bag cavity. The aperture (13) is surrounded by a flange (12) and may be provided in any shape or size, such as circular, oblong, heart shaped and may be symmetrical or asymmetrical, preferably the aperture has an oblong configuration either in the longitudinal or in the transversal direction, most preferably the contours of the aperture are in the shape of two ellipses with the respective main axes being substantially perpendicular.

The flange (12) is attached to the bag (11) according to any means known to the man skilled in the art which may provide permanent or releasable attachment. Preferably however, the flange (12) is attached to the bag (11) by adhesive. Typically, the bag (11) will be attached to the flange (12), towards the outer periphery of flange (12) so as not to cause any obstruction for the entering liquids.

The flange (12) may be provided in any size depending on the wearer group for which the device is intended. Similarly the flange (12) may be provided in any shape and preferably has a symmetrical shape preferably comprising a plurality of lobes (16).

The flange comprises a garment facing portion (21) and a wearer facing portion (22). In an preferred embodiment these are two large, substantially flat surfaces.

The flange (12) should be made of soft, flexible and malleable material to allow easy placement of the flange to the uro genital area. In addition it is preferred that the flange (12) be made of a hydrophobic material such that if urine does come into contact with the perimeter (30) surrounding the aperture (13) it is repelled and does not wick to the outer edge (32) of the flange (12). Typical materials include nonwoven materials, wovens, open celled thermoplastic foams, closedell thermoplastic foams, composites of open celled foams and stretch nonwoven, and films. A closed-cell foam of polyethylene has been found effective, but more preferably an open celled polyurethane foam is used. Preferably, such foams have a thickness within the general range of 0.1 to 5 millimeters and a density of 5 to 250 g/m$^2$, more preferably 50 g/m$^2$. Other thermoplastic foam materials, or other suitable plastics sheet materials having the described properties of such foams (i.e., softness, pliability, stretchability, and contractability) might also be used. Preferably, the material of garment facing surface (21) of the flange (12) may extend into the defined aperture area so as to form a skirt or flap of material which prevents unintentional adhesion of the surface edges of the flange (12) defining the aperture (13) to oneanother during use.

According to the present invention the urine management device (10) further comprises an attachment means to secure the device to the wearer. Such means include straps and more preferably comprises a body-compatible pressure sensitive adhesive (20) applied to the wearer facing portion (42) of the flange (12).

The adhesive (20) is preferably covered with a release means (not shown) in order to protect the adhesive (20) such as siliconized paper. The adhesive (20) can cover the entire wearer facing surface of the flange or more preferably have at least one, preferably two to six non-adhesive portions. These portions may be adhesive free or may contain inactivated or covered adhesives. As is evident from FIG. 1, the adhesive is in one preferred embodiment not applied to the entire wearer facing surface area of the flange (12), so as to provide lobes (16) on either side of the flange (12) which are non-adhesive and can thereby serve to facilitate placement and removal of the device whilst avoiding contact with the adhesive. These lobes are however preferably also covered by the release means. Before application of the urine management device (10) to the skin of the wearer, the release means if present is removed. Alternatively a single lobe placed centrally about the longitudinal axis of the flange (12) is also particularly beneficial.

According to the present invention any medically approved water resistant pressure sensitive adhesive may be used to attach the device to the uro-genital area of the wearer, such as hydrocolloid adhesives and hydrogel adhesives. Particularly effective adhesives in providing the desired adhesive properties to secure the flange to the skin of the wearer at the sensitive uro-genital area, whilst allowing for relatively painless application and removal, are formed from crosslinking polymers with a plastisicer to form a 3-dimensional matrix.

Suitable adhesives for use herein are hydrogel adhesives available from 3M and Promeon.

The adhesive (20) can be applied to the wearer facing surface (42) of the flange (12) by any means known in the art such as slot coating, spiral, or bead application or printing. Typically the adhesive (20) is applied at a basis weight of from 20 g/m$^2$ to 2500 g/m$^2$, more preferably from 500 g/m$^2$ to 2000 g/m$^2$ most preferably from 700 g/m$^2$ to 150 g/m$^2$ depending on the end use envisioned. For example for urine management devices (10) to be used for babies the amount of adhesive (20) may be less than for urine management devices designed for active adult incontinence sufferers.

According to another aspect of the present invention, the urine management device (10) has been found particularly useful and beneficial when utilised in conjunction with a garment or a disposable diaper and/or a faecal management device. Typically the urine management device will be positioned to the uro-genital area of the wearer positioned and secured to the wearer by the adhesive flanges and patches of adhesives. Subsequently, the diaper is positioned over the urine management device (10) and fastened in a conventional manner around the body of the wearer. It has been found that in addition to providing excellent separation between urine and faecal matter, the combined urine management device (10) and diaper system reduce skin irritation, which may at time occur, especially as the wearer group includes the very old, young and unhealthy wearers.

What is claimed is:

1. A female adult urine management device (10) comprising a bag (11), said bag (11) having an aperture and a flange (12) surrounding said aperture for adhesive attachment to the uro genital area of wearer, said flange (12) being attached to said bag (11) wherein said flange comprises an outer periphery (44), and an inner periphery (45) adjacent said aperture, a longitudinal centreline (L) and a transverse centreline (T) orthogonal thereto, said transverse centreline (T) segmenting said anatomically-shaped flange (12) into a front portion (46) and a rear portion (47), said flange having a wearer facing surface (43) and a garment facing surface (42), wherein said wearer facing surface (43) of said flange (12) comprises a projection (48) in said rear portion (46).

2. A female adult urine management device (10) according to claim 1 wherein said projection (48) is disposed between said outer periphery (44) and said inner periphery (45) of said flange (12) in a direction parallel to said longitudinal direction (L).

3. A female adult urine management device (10) according to claim 2 wherein said projection (48) extends from said outer periphery (44) to said inner periphery (45).

4. A female adult urine management device (10) according to claim 1 wherein said projection (48) is symmetrical about said longitudinal axis.

5. A female adult urine management device (10) according to claim 1 wherein said projection (48) has an effective height ranging from 5 millimeters to 30 millimeters, a width ranging from 3 millimeters to 20 millimeters and a length ranging from 5 millimeters to 40 millimeters.

6. A female adult urine management device (10) according to claim 5 wherein said projection (48) has an effective height ranging from 10 millimeters to 20 millimeters, a length from 15 millimeters to 25 millimeters and a width 5 millimeters to 10 millimeters.

7. The use of a female adult urine management device (10) according to claim 1 wherein said projection (48) is provides a seal to prevent leakage from said device.

8. The use of a female adult urine management device (10) according to claim 1 wherein said projection (48) is adapted to fit between the labia and the anus of a female wearer.

9. The use of a female adult urine management device (10) according to claim 7 having said projection (48) as an application aid to ensure ease of placement and ideal positioning of said device.

10. The use of a female adult urine management device (10) according to claim 1, wherein said projection (28) prevents urinary tract infections.

* * * * *

UNITED STATES PATENT AND TRADEMARK OFFICE
CERTIFICATE OF CORRECTION

PATENT NO. : 6,551,292 B1
DATED : April 22, 2003
INVENTOR(S) : D'Acchioli et al.

It is certified that error appears in the above-identified patent and that said Letters Patent is hereby corrected as shown below:

<u>Column 6,</u>
Line 24, delete "spuniaced" and insert -- spunlaced --.

<u>Column 9,</u>
Line 22, delete "closedell" and insert -- closed-cell --.

Signed and Sealed this

First Day of June, 2004

JON W. DUDAS
*Acting Director of the United States Patent and Trademark Office*